United States Patent
Alla et al.

[11] Patent Number: 6,000,398
[45] Date of Patent: Dec. 14, 1999

[54] SPRING ACTION MALE CONDOM

[76] Inventors: Ravikumar Alla; Madhusudhan Alla; Raghunatha Alla; Alla V. K. Reddy, all of 9 Webster Ct., Plainsboro, N.J. 08536

[21] Appl. No.: 09/186,797

[22] Filed: Nov. 5, 1998

Related U.S. Application Data

[62] Division of application No. 08/975,619, Nov. 21, 1997, Pat. No. 5,836,308.

[51] Int. Cl.$^6$ ....................................................... A61F 6/04
[52] U.S. Cl. ........................................... 128/844; 128/918
[58] Field of Search ..................................... 128/842, 844, 128/918; 604/347–353

[56] References Cited

U.S. PATENT DOCUMENTS

| | | |
|---|---|---|
| D. 246,119 | 10/1977 | Okamoto .................................. D24/99 |
| D. 253,009 | 9/1979 | Okamoto .................................. D24/99 |
| D. 254,808 | 4/1980 | Meldahl . | 
| 2,586,674 | 2/1952 | Lonne ...................................... 128/844 |
| 3,463,141 | 8/1969 | Mozolf . |
| 3,536,066 | 10/1970 | Ludwig . |
| 4,004,591 | 1/1977 | Freimark . |
| 4,798,660 | 1/1989 | Meadows . |
| 5,027,831 | 7/1991 | Reddy . |
| 5,082,004 | 1/1992 | Reddy . |
| 5,176,152 | 1/1993 | Wheeler . |
| 5,538,584 | 7/1996 | Metz . |

*Primary Examiner*—Michael A. Brown
*Attorney, Agent, or Firm*—Reising, Ethington, Barnes, Kisselle, Learman & McCulloch, P.C.

[57] ABSTRACT

A spring on spring condom has one spring action established by the elasticity of the condom material and the spring on spring condom has another spring action established by a spring formation on the condom that is attributable to a combination of the shape of the spring formation and the elasticity of the condom material; a method for forming the condom includes the steps of providing a mold having a spring shape on the exterior of a dipping mold adjacent the end thereof and dipping the mold into an elastomeric material for forming a thin layer of material thereover that when removed from the mold will have the configuration of a spring on spring condom.

7 Claims, 3 Drawing Sheets

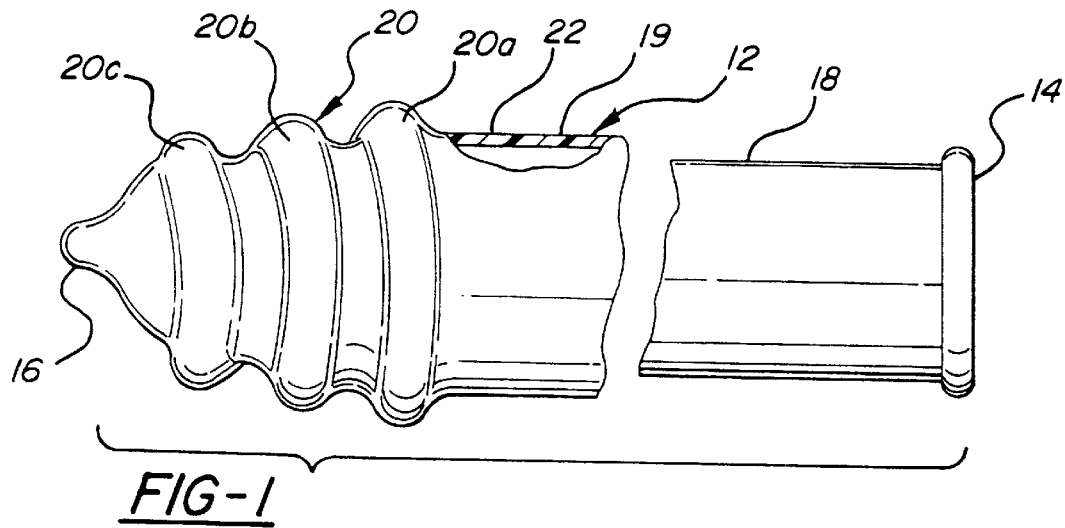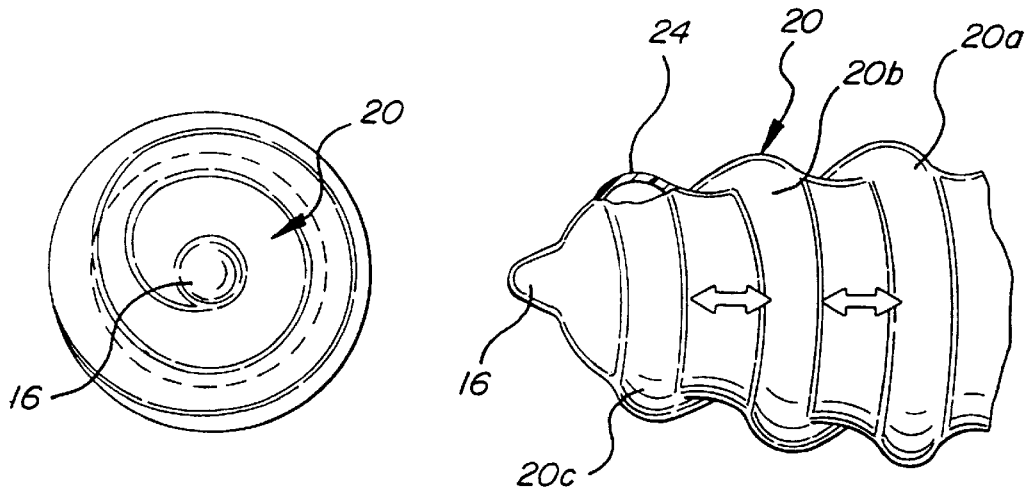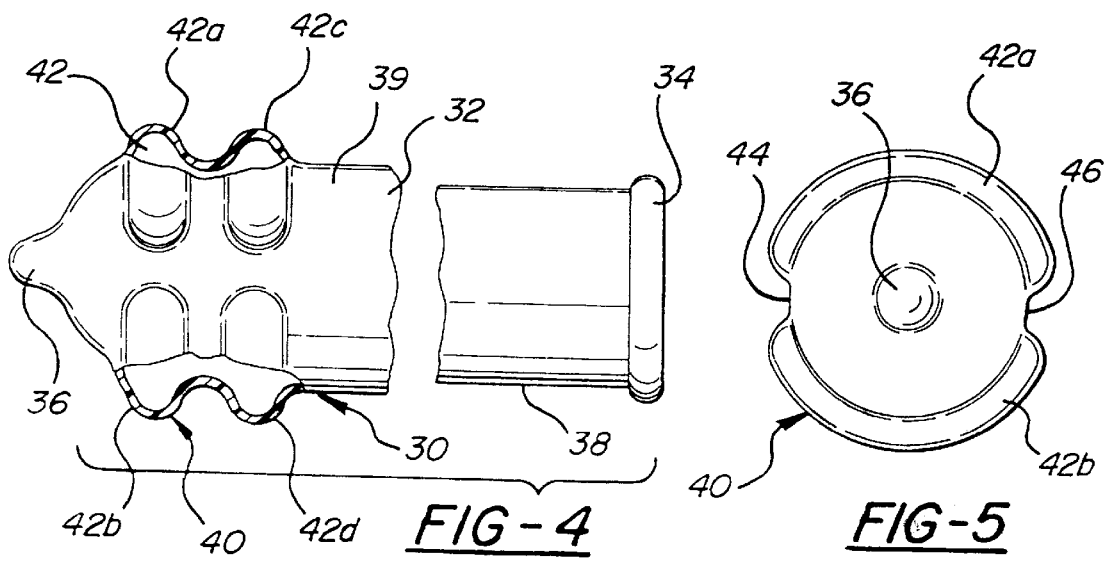

SPRING ACTION MALE CONDOM

This is a division of application Ser. No. 08/975,619 filed on Nov. 21, 1997, now U.S. Pat. No. 5,836,308.

FIELD OF THE INVENTION

This invention relates to prophylactic devices and more particularly to male condoms.

BACKGROUND OF THE PRIOR ART

The AIDS epidemic has caused more people to consider the use of condoms for protection against transmission of viral and bacterial diseases. In order to assure protection the wall thicknesses of the condoms have been increased to assure that there will be no pin hole openings therein for transmission of bodily fluids carrying the disease vectors. Such protection however can reduce sensitivity and user sensation to a point where the alternative of no protection might be encouraged.

Various types of male condoms have been proposed in which rings or other formations are formed on the sheath of the condom for physiological stimulation by a female during use.

Examples of such condoms are shown in U.S. Pat. Nos. 4,004,591 and 3,536,066 wherein loose fitting condoms are used to enhance use. Other proposals include U.S. Design Pat. No. 254,808 wherein outwardly directed bulges are illustrated.

U.S. Pat. Nos. 5,027,831 and 5,082,004 disclose arrangements wherein bulges are formed to move into an out of the condom sheath to enhance male stimulation during use.

None of these arrangements provide for a spring configuration on the condom that will move relative to the condom to enhance stimulation to both males and females at the same time.

STATEMENT OF THE INVENTION AND ADVANTAGES

The problem with prior art arrangements is that the various formations on the sheath of the condom have been configured for stimulation for one user. There has been no provision where the condom itself has a spring action built into its configuration that will act to pleasure both the male and female during coitus.

Accordingly, an object of the present invention is to provide a male condom, which will be more acceptable to both a male and female during use.

A feature of the present invention is to provide an elastic male condom that has a feature thereon that will produce spring action independently of user action.

A further feature of the present invention is to provide a spring on spring condom.

Yet another feature of the present invention is to provide a condom that can be fit on a user and that will be positioned during use to cause a portion thereof to have a spring action independent of the fitting of the condom on a user.

A further object is to provide for conjoint pleasure by the provision of a formation on the sheath of a male condom that will act as a spring that will actively position the formation between an extended position and a retracted position independently of any user action.

Still another feature of the invention is to provide a spring on spring condom wherein one spring action is established by the elasticity of the condom material and wherein another spring action is established by a spring formation on the condom that is attributable to a combination of the shape of the spring formation and the elasticity of the condom material.

Another object of the invention is to provide such spring action by providing an integrally formed series of convolutions or channels in the end of the male condom that are arranged to be extended during use from a retracted position to an extended position wherein the integrally formed series of channels exert a return spring force that will move the channels independently of user action back to the retracted position.

A further feature is to provide for such convolutions or channels formed in a helical shape near the closed end of the condom.

A further feature is to provide such convolutions or channels formed as a series of circumferentially spaced segments that are axially spaced from a second series of circumferentially spaced segments and wherein longitudinal separation bands have a retracted position to maintain a first position of the circumferentially spaced segments and an extended stressed position when the circumferentially spaced segments are pulled apart during use that will act to return the segments to their retracted position.

A further feature is to provide such circumferentially spaced segments as opposed pairs of arcuate segments.

A still further feature is to provide such circumferentially spaced segments as arcuate segments staggered on opposite sides of the circumference of the condom.

Yet another feature is to provide such circumferentially spaced segments as arcuate segments staggered on opposite sides of the circumference of the condom at staggered locations along the length of the condom.

A still further feature is to provide such channels as a series of sinusoidal shapes formed around the tip of the condom and that are expandable into an extended stressed position and wherein the sinusoidal shapes act to return the shapes to an unstressed retracted position.

A still further object of the present invention is a method for forming a male condom including the steps of providing a condom having anyone of the aforesaid spring shapes on the exterior of a dipping mold adjacent the end thereof and dipping the mold into an elastomeric material for forming a thin layer of material thereover that when removed from the mold will have the configuration of anyone of the embodiments of the spring on spring condoms of the present invention.

Other advantages of the present invention will be readily appreciated, as the same become better understood by reference to the following detailed description when considered in connection with the accompanying drawings wherein:

BRIEF DESCRIPTION OF THE DRAWINGS

FIG. 1 is a side elevational view of one embodiment of the invention showing a helically shaped spring on the end of an elastic spring sheath of a male condom;

FIG. 2 is an end elevational view of the embodiment in FIG. 1 looking in the direction of the arrows;

FIG. 3 is a view of the helically shaped spring in an extended stressed position and showing a relative unstressed retracted position thereof;

FIG. 4 is a side elevational view of another embodiment of the invention showing a circumferentially and longitudinally spaced arcuate shaped spring on the end of an elastic spring sheath of a male condom;

FIG. 5 is an end elevational view of the embodiment in FIG. 1 looking in the direction of the arrows;

DETAILED DESCRIPTION OF PREFERRED EMBODIMENTS

Figure 6:
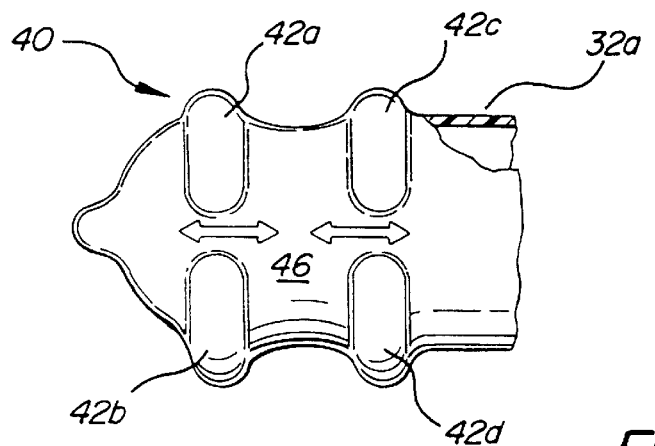
FIG. 6 is a view of the arcuate shaped spring in an extended stressed position and showing a relative unstressed retracted position thereof.

FIG. 1 discloses a male condom having a tubular pouch or sheath 12 with an open end 14 and a closed end 16. The pouch has a small diameter segment 18 formed from the open end 14 and an increased diameter segment 19 to a point adjacent a helically shaped spring 20 adjacent the closed end 18.

In accordance with one aspect of the invention, the wall 22 of the sheath 12 has an elasticity that will enable the condom to be fit on a user and is therefor a first spring because of such elasticity. The spring 20 provides a second spring action in the condom that will actively position between an extended position back to a retracted position. The spring 20 is formed integrally with the wall 22 and in the first embodiment is shaped as a helical spring having a channel sectioned convolutions 24 therein that extend radially outwardly of the wall 22 and are wound about the wall so as to form an additional spring action therein as will be discussed.

The wall 22 and the convolutions 24 are thin membranes that enhance sensation during use but are of sufficient strength and impermeability to prevent wall separations or pinprick hole configurations that might enable fluid transmission thereacross during use. Thus the wall 22 and the convolutions 24 thereon act to provide protection against AIDS or other social diseases.

Additionally, the convolutions 24 having a normally unstressed, axially retracted position shown in FIG. 1. When the condom is stretched axially, the convolutions assume a second extended stressed position shown in FIG. 3 wherein the coils 20a, 20b, 20c of the helical spring 20 are parted from one another so as to impose a spring bias action that will return the spring 20 back to its normally, unstressed, axially retracted position. Hence, in use, the male condom 10 can be said to be an "active" condom that will, by itself, have the potential for imparting an axially directed (vis-à-vis the length of the condom) pleasurable stroking action to both the male and female during coitus.

Yet another feature of the present invention is to provide a condom that can be fit on a user and that will be positioned during use to cause a portion thereof to have a spring action independent of the fitting of the condom on a user.

Thus, the embodiment of FIGS. 1–3 provides for such conjoint pleasure by the provision of an end formation on the sheath of a male condom, e.g., the convolutions 24 that will act as a spring for actively positioning the formation from an extended position caused by user actions back to a retracted position when released. Furthermore, in the embodiment of FIGS. 1–3 such spring action of the convolutions constitutes a "spring on spring" condom wherein one spring action is established by the elasticity of the condom material and wherein another spring action is established by a spring formation on the condom that is attributable to a combination of the shape of the spring formation and the elasticity of the condom material. The increased diameter segment 19 separates the condom slightly from the user so that the spring on spring action will not be inhibited by too tight a fit.

FIG. 4 discloses a male condom 30 having a tubular pouch or sheath 32 with an open end 34 and a closed end 36. The pouch has a small diameter segment 38 formed from the open end 34 to a large diameter segment 39 to a point adjacent a second spring 40 formed by an integrally formed series of convolutions 42 in the end of the male condom that are arranged to be extended during use from a retracted position to an extended position wherein the integrally formed series of convolutions 42 are arranged on the end of the condom 30 to exert a return spring force that will move the convolutions back to the retracted position. In the embodiment of FIG. 4, such series of convolutions 42 have a channel section and are formed as a first series of circumferentially spaced segments 42a–42b. The segments 42a–42b are axially spaced from a second series of circumferentially spaced segments 42c–42d and longitudinal separation bands 44 and 46 are provided at the spaces between the segments. The bands 44, 46 have a retracted position to maintain the circumferentially spaced and axially arranged segments 42a–42d in a first unstressed or retracted position on the end of the male condom 30. The bands 44, 46 have an extended stressed position wherein the circumferentially spaced segments 42a–42b are pulled apart from the segments 42c–42d during use. The bands 44, 46 act to return the segments to their retracted position independently of user movement.

As in the first embodiment, the wall 32a of the small diameter segment 38 and the large diameter segment 39 has an elasticity that will enable the condom to be fit on a user and is therefor a first spring because of such elasticity. The spring 40 provides a second spring action in the condom that will actively position the extended position caused by user actions back to a retracted position independently of any user action. The spring 40 is formed integrally with the wall 32a and as in the first embodiment the convolutions 42 extends radially outwardly of the wall 32a and are spaced circumferentially and axially about the wall so as to form an additional spring action therein like in the first embodiment of FIGS. 1–3. The large diameter segment 39 separates the condom slightly from the user so that the spring on spring action will not be inhibited by too tight a fit.

As in the first embodiment of FIGS. 1–3, the embodiment of FIGS. 4–6 have convolutions 42 and a wall 32a that are thin membranes that enhance sensation during use but are of sufficient strength and impermeability to prevent wall separations or pin prick hole configurations that might enable fluid transmission thereacross during use. Thus the wall 32a and the convolutions 42 thereon act to provide protection against AIDS or other social diseases.

The convolutions 42 have a normally unstressed, axially retracted position shown in FIG. 4. When the condom 30 is stretched axially, the convolutions assume a second extended stressed position shown in FIG. 6 wherein the segments 42a–42b are parted from the segments 42c–42d and the bands 44, 46 are stretched to impose a spring bias action that will return the spring 40 back to its normally, unstressed, axially retracted position. Hence, in use, the male condom 30 can be said to be an "active" condom that will by itself have the potential for imparting an axially directed (vis-à-vis the length of the condom) pleasurable stroking action to both the male and female during coitus, independently of any user movement in the direction of the axially retracted position. Thus, the embodiment of FIGS. 4–6 provides for such conjoint pleasure by the provision of an end formation on the sheath of a male condom, e.g., the convolutions 42 and bands 44, 46 that will act as a spring for actively positioning the formation from an extended position caused by user actions back to a retracted position independently of any user action. Furthermore, in the embodiment of FIGS. 4–6, as in the case of the embodiment of FIGS. 1–3 such spring action of the convolutions 42 and bands constitutes a "spring on spring" condom wherein one spring action is established by the elasticity of the condom material and wherein another spring action is established by a spring formation on the condom that is attributable to a combination of the shape of the spring formation and the elasticity of the condom material.

Figure 7:
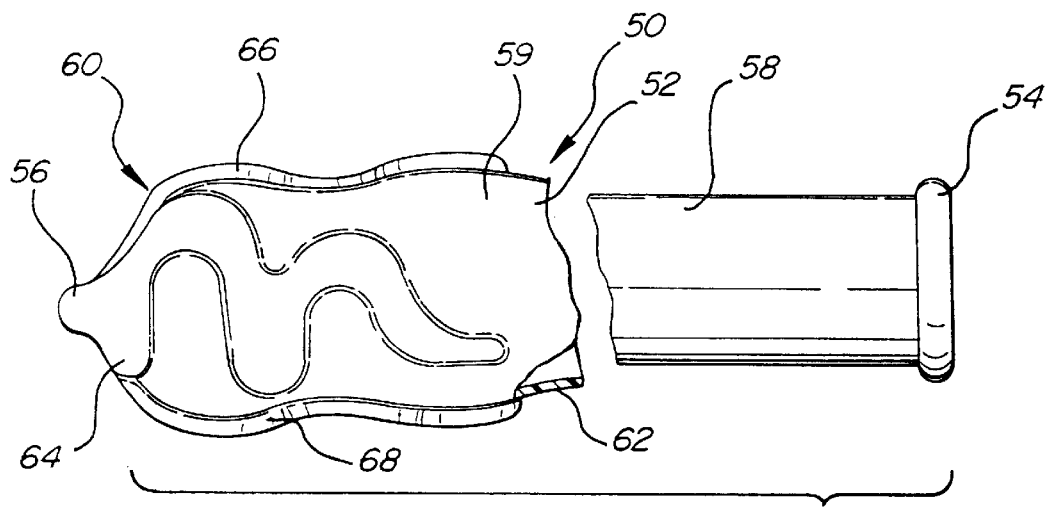
FIG. 7 is a side elevational view of another embodiment of the invention showing a sinusoidally shaped spring on the end of an elastic spring sheath of a male condom.
Figures 8, 9:
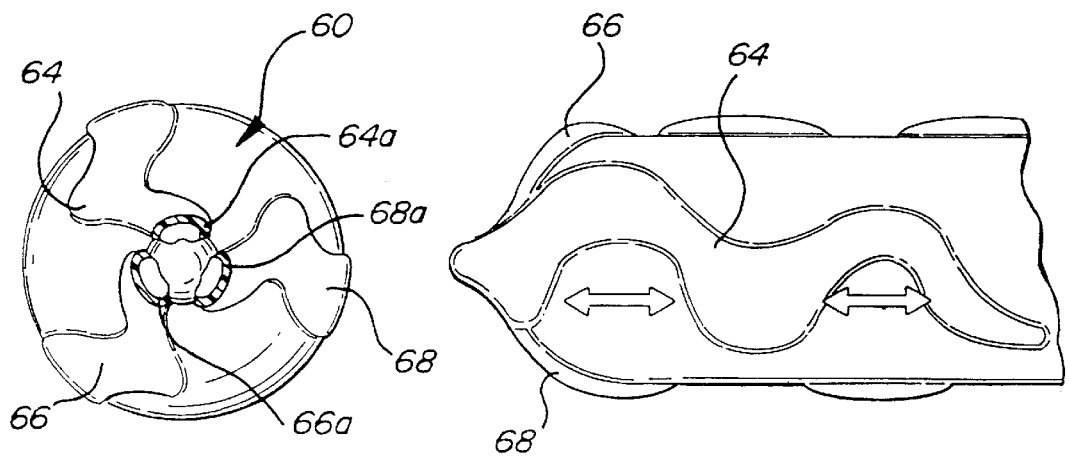
FIG. 8 is an end elevational view of the embodiment in FIG. 7 looking in the direction of the arrows.
FIG. 9 is a view of the sinusoidal spring in an extended stressed position and showing a relative unstressed retraction position thereof.

FIGS. 7–9 discloses a male condom 50 having a tubular pouch or sheath 52 with an open end 54 and a closed end 56. The pouch has a small diameter segment 58 formed from the open end 54 to a large diameter segment 59 to a point adjacent a sinusoidally shaped spring 60 adjacent the closed end 56.

In accordance with one aspect of the invention, the wall 62 of the constant diameter segment has an elasticity that will enable the condom to be fit on a user and is therefor a first spring because of such elasticity. The spring 60 provides a second spring action in the condom that will actively position the between an extended position caused by user actions back to a retracted position independently of any user action. The spring 60 is formed integrally with the wall 62 and as in the first embodiment is shaped so as to provide convolutions 64–68 formed as channels 64a–68a each having a sinusoidal shape formed around the tip of the condom and that are expandable into a extended stressed position wherein the sinusoidal shapes act to return the shapes to an unstressed retracted position. The convolutions 64–68 extend radially outwardly of the wall 62 and are wound about the wall so as to form an additional spring action therein as will be discussed.

The wall 62 and the convolutions 64–68 are thin membranes that enhance sensation during use but are of sufficient strength and impermeability to prevent wall separations or pinprick hole configurations that might enable fluid transmission thereacross during use. Thus the wall 62 and the convolutions 64–68 thereon act to provide protection against AIDS or other social diseases. The large diameter segment 59 separates the condom slightly from the user so that the spring on spring action will not be inhibited by too tight a fit.

Additionally, the convolutions 64–68 having a normally unstressed, axially retract position shown in FIG. 7. When the condom is stretched axially, the convolutions assume a second extended stressed position shown in FIG. 9 wherein the sinusoidally shaped coils 64–68 of the spring 60 are formed to have a greater spacing between the peaks and valleys of the sinusoidal shape so as to impose a spring bias action that will return the spring 60 back to its normally, unstressed, axially retracted position. Hence, in use, the male condom 50 can be said to be an "active" condom that will, by itself, have the potential for imparting an axially directed (vis-à-vis the length of the condom) pleasurable stroking action to both the male and female during coitus as the sinusoidally shaped convolutions move relative to the male and female as they are reshaped into their retracted position when released in the direction of the axially retracted position. Yet another feature of the present invention is to provide such a condom that can be fit on a user and that will be positioned during use to cause a portion thereof to have a spring action independent of the fitting of the condom on a user.

Thus, the embodiment of FIGS. 7–9 provides for such conjoint pleasure by the provision of an end formation on the sheath of a male condom, e.g., the convolutions 64–68 that will act as a spring for actively positioning the formation from an extended position caused by user actions back to a retracted position independently of any user action. Furthermore, in the embodiment of FIGS. 7–9 such spring action of the convolutions constitutes a "spring on spring" condom wherein one spring action is established by the elasticity of the condom material and wherein another spring action is established by a spring formation on the condom that is attributable to a combination of the shape of the spring formation and the elasticity of the condom material.

Figure 10:
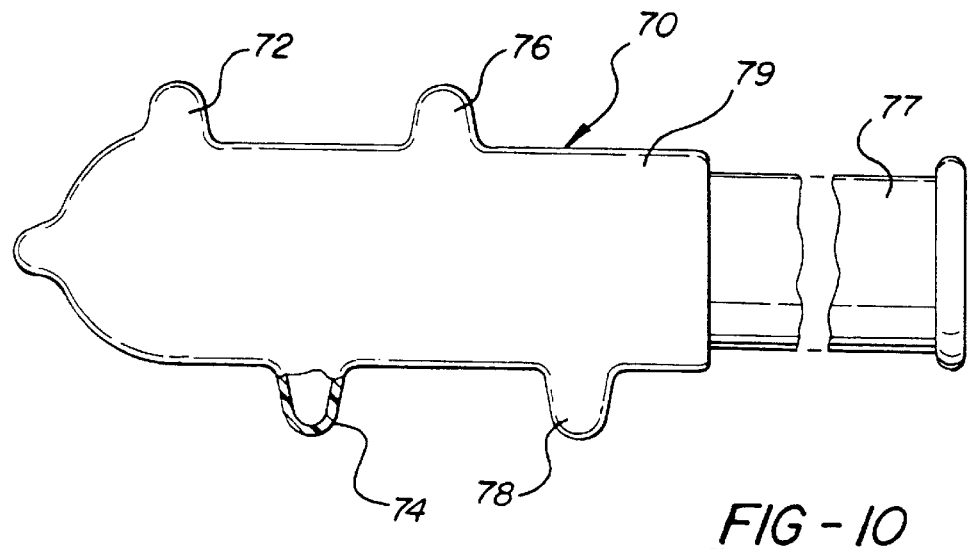
FIG. 10 is a view of an embodiment having circumferentially spaced segments as arcuate segments staggered on opposite sides of the circumference of the condom.

In the embodiment of FIG. 10, a male condom 70 is provided having the shape and convolutions that comprise a series of circumferentially spaced segments that are axially spaced from a second series of circumferentially spaced segments and wherein longitudinal separation bands have a retracted position to maintain a first position of the circumferentially spaced segments and an extended stressed position when the circumferentially spaced segments are pulled apart during use that will act to return the segments to their retracted position. In this embodiment, however the circumferentially spaced segments are formed as arcuate convolutions or channels 72–78 as in the case of prior embodiments (in this embodiment one-half circles) but with it being understood that lesser arcuate shapes are also contemplated. Each of the half circles are staggered on opposite sides of the circumference of the condom. As in the previous embodiments the sheath is provided with a small diameter segment 77 and a large diameter segment 79.

Figure 11:
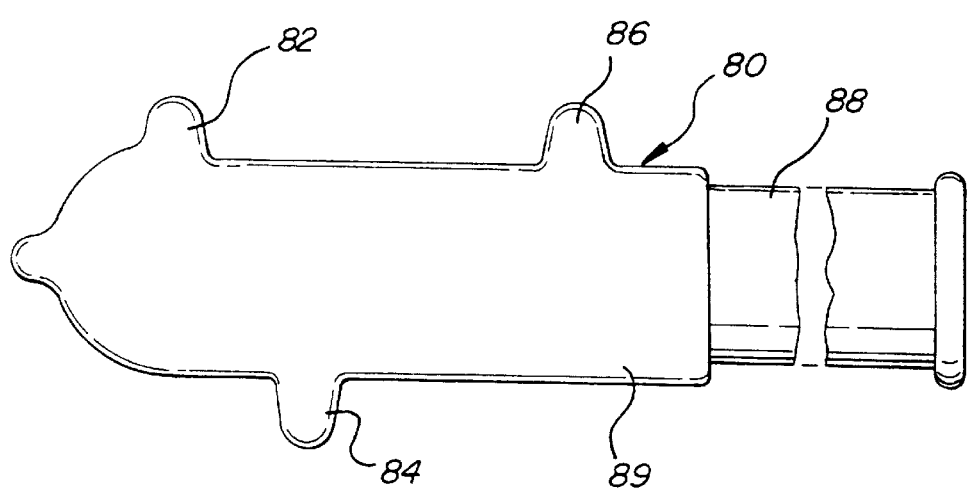
FIG. 11 is a view of an embodiment having circumferentially spaced segments as arcuate segments staggered on opposite sides of the circumference of the condom at staggered locations along the length of the condom.
Figure 12:
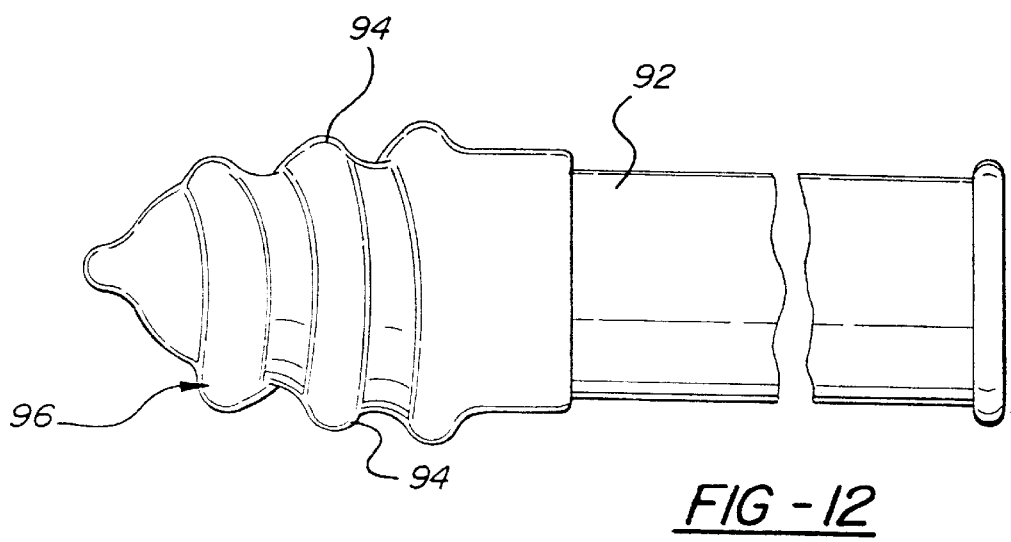
FIG. 12 is a view of one embodiment of a mold for practicing the method of the present invention.

In the embodiment of FIG. 11 a male condom 80 is shown with circumferentially spaced segments that are arcuate segments 82, 84, 86 staggered on opposite sides of the circumference of the condom at different spaced locations along the length of the condom. The sheath has a small diameter segment 88 and a large diameter segment 89.

The method of the present invention includes the steps of providing a mold 90 having an elongated cylindrical portion 92 and an outer surface 94 on one end thereof defining a convolution 96 thereon defining a spring formation; dipping said mold into a liquid elastomeric material to form a thin elastic membrane having a first spring action and forming a pouch with an open end and a closed end with a tubular wall formed therebetween and including a convolution shaped in the form of the convolution on said mold and formed integrally of said tubular wall adjacent said closed end that will produce spring movement independently of the elasticity of the elastomeric material. Tracking the embodiments of male condom inventions described above, the method also contemplates the steps of providing a mold having anyone of the following configurations; a mold that is provided with a convolution having a helical shaped outer surface defining a spring formation; a mold that is provided with a series of circumferentially spaced surface segments that are axially spaced from a second series of circumferentially spaced surface segments to form the spring formation; a mold that is provided with circumferentially spaced surface segments formed as arcuate segments staggered on opposite sides of the circumference of the mold to form the spring formation; a mold that is provided with circumferentially spaced surface segments that are arcuate segments staggered on opposite sides of the circumference of the mold at staggered locations along the length of the mold to form the spring formation and a mold that is provided with surface convolutions forming a series of sinusoidal shapes formed around the tip of the mold to form the spring formation.

In the present invention the condom and the elastic material from whence it is made can be of material having an elastic impermeable characteristic once shaped and removed from the mold. Examples of such materials include substances such as natural rubber (e.g. latex); synthetic rubber (e.g. silicone rubber); polyurethane; and other elastic substances such as thermoplastic polyolefin elastomers.

While the invention has been described in an illustrative manner it should be understood that the invention may be practiced other than as specifically described herein and yet remain within the scope of the appended claims.

What is claimed is:

1. A male condom comprising an elongated tubular portion formed by a thin elastic membrane having a first spring action and forming a pouch with an open end and a closed end with a tubular wall formed therebetween and having a convolution formed integrally of said tubular wall adjacent said closed end characterized by:

said convolution configured radially outwardly of said tubular portion to act as a spring that will actively position the convolution from an extended position axially of said tubular portion caused by user actions back to a retracted position when released for moving said convolution to produce a stroking action that will provide for both male and female pleasure;

and said tubular portion having an increased diameter at said convolution to separate the condom from a user so that the spring action of said condom will not be inhibited.

2. The male condom of claim 1 further characterized by said convolutions being integrally formed channels in the end of the male condom that are arranged to be extended during use from a retracted position to an extended position wherein the integrally formed series of channels exert a return spring force that will move the channels when released back to the retracted position.

3. The male condom of claim 1 wherein said convolution has a helical shape near the closed end of the condom.

4. The male condom of claim 1 wherein said convolution comprises a series of circumferentially spaced segments that are axially spaced from a second series of circumferentially spaced segments and wherein longitudinal separation bands have a retracted position to maintain a first position of the circumferentially spaced segments and an extended stressed position when the circumferentially spaced segments are pulled apart during use that will act to return the segments to their retracted position.

5. The male condom of claim 4 wherein said circumferentially spaced segments are arcuate segments staggered on opposite sides of the circumference of the condom.

6. The male condom of claim 4 wherein said circumferentially spaced segments are arcuate segments staggered on opposite sides of the circumference of the condom at staggered locations along the length of the condom.

7. The male condom of claim 1 wherein said convolution comprises a series of sinusoidal shapes formed around the tip of the condom and that are expandable into a extended stressed position wherein the sinusoidal shapes act to return the shapes to an unstressed retracted position.

* * * * *